United States Patent [19]
Smith

[11] 3,946,324
[45] Mar. 23, 1976

[54] ISOLATION AMPLIFIER
[75] Inventor: Lewis R. Smith, Sudbury, Mass.
[73] Assignee: Analog Devices, Incorporated, Norwood, Mass.
[22] Filed: Nov. 7, 1974
[21] Appl. No.: 521,930

Related U.S. Application Data
[63] Continuation of Ser. No. 379,804, July 16, 1973, abandoned, which is a continuation of Ser. No. 181,344, Sept. 17, 1971, abandoned.

[52] U.S. Cl. ................................................. 330/10
[51] Int. Cl.² .......................................... H03F 3/38
[58] Field of Search ........................................ 330/10

[56] References Cited
UNITED STATES PATENTS

| | | | |
|---|---|---|---|
| 2,205,075 | 6/1940 | Wilhelm | 333/77 |
| 3,156,859 | 11/1964 | Cox | 321/8 |
| 3,196,364 | 7/1965 | Latham, Jr. | 330/68 |
| 3,405,366 | 10/1968 | Philbrick | 330/7 |

Primary Examiner—James B. Mullins
Attorney, Agent, or Firm—Parmelee, Johnson & Bollinger

[57] ABSTRACT

An isolation amplifier comprising three separate, conductively-isolated sections: (1) an input section including an AC modulator, (2) an output section including a demodulator, and (3) an oscillator section. The AC signal from the oscillator section is transformer-coupled to the modulator section to provide the AC carrier excitation for the modulator and also to energize a rectifier power supply circuit to produce DC voltages for the active elements of the input section. The modulated carrier signal developed by the modulator section is transformer-coupled to the demodulator section. Each of the transformers includes two separate cores which are coupled inductively by single-turn windings. Special electrostatic shielding is provided to reduce leakage effects.

7 Claims, 3 Drawing Figures

ISOLATION AMPLIFIER

This is a continuation of application Ser. No. 379,804 filed July 16, 1973, and now abandoned, which in turn is a continuation of Ser. No. 181,344 filed Sept. 17, 1971, and now abandoned.

This invention relates to solid-state electronic amplifiers. More particularly, this invention relates to isolation amplifiers having no DC conductive paths between the input terminals and any of the surrounding ground, output, or power supply circuits. This invention also relates to such amplifiers including circuit features to minimize leakage or other undesired current flow to or through any signal source connected to the amplifier input terminals.

Amplifiers have in the past been provided with circuit arrangements for effecting conductive isolation between different components or elements connected thereto. Although such amplifiers have served useful functions in some fields, typically they have not been capable of meeting the severe requirements of a number of unique and important applications. One such important application is in the medical field where for a variety of purposes electronic equipment must be connected to human patients to measure electrical impulses and the like, e.g. for taking electrocardiograms. It has become increasingly apparent that conventional electronic equiupment can, when connected to a human, cause serious injury or even death in the event of minor equipment malfunctions, operator error, or some other inadvertent event.

The danger is particularly acute in heart surgery where metallic catheters frequently are inserted through arteries or veins directly into the heart interior. It has become apparent that if even tiny leakage currents flow through such a probe and into the heart muscles, patient death by electrocution can be expected to result. For example, voltages as low as 10 millivolts can send currents of 20 microamps through the heart and cause death by micro-shock.

There are many other applications for high-performance isolation amplifiers. For example, in the field of industrial process control, signal sources often must be floated above ground, and it becomes necessary to isolate the signal source from the system output because the output signal frequently must be connected to devices which have a conductive path to ground. In such applications, the flow of very small leakage currents introduces measurement errors which can prevent proper functioning of the process control system.

Thus, for numerous applications, an isolation amplifier must not only meet rigorous noise, drift, and common mode specifications, but in addition, must offer stringent isolation performance which is fail-safe under various kinds of abnormal operational conditions encountered from time to time. In one embodiment of the invention, to be described hereinbelow in detail, an amplifier is provided which has $10^{12}$ ohms input-to-ground resistive isolation, can withstand 1000 volts (continuously) of common mode voltage without breakdown, resumes read-out of tiny signals within 200 milliseconds of a 5000 volt transient pulse, provides a 20 megohm fail-safe resistance between input terminals, and, when used with a human patient as a signal source, limits patient leakage currents well below the 20 microamps danger level.

Accordingly, it is a general object of this invention to provide a superior high-performance isolation amplifier. A more specific object of this invention is to provide such an amplifier which is especially adapted to be manufactured at relatively modest costs. Other more specific objects, aspects and advantages of the invention will in part be pointed out in, and in part apparent from, the following description considered together with the accompanying drawings in which.

Figure 1:
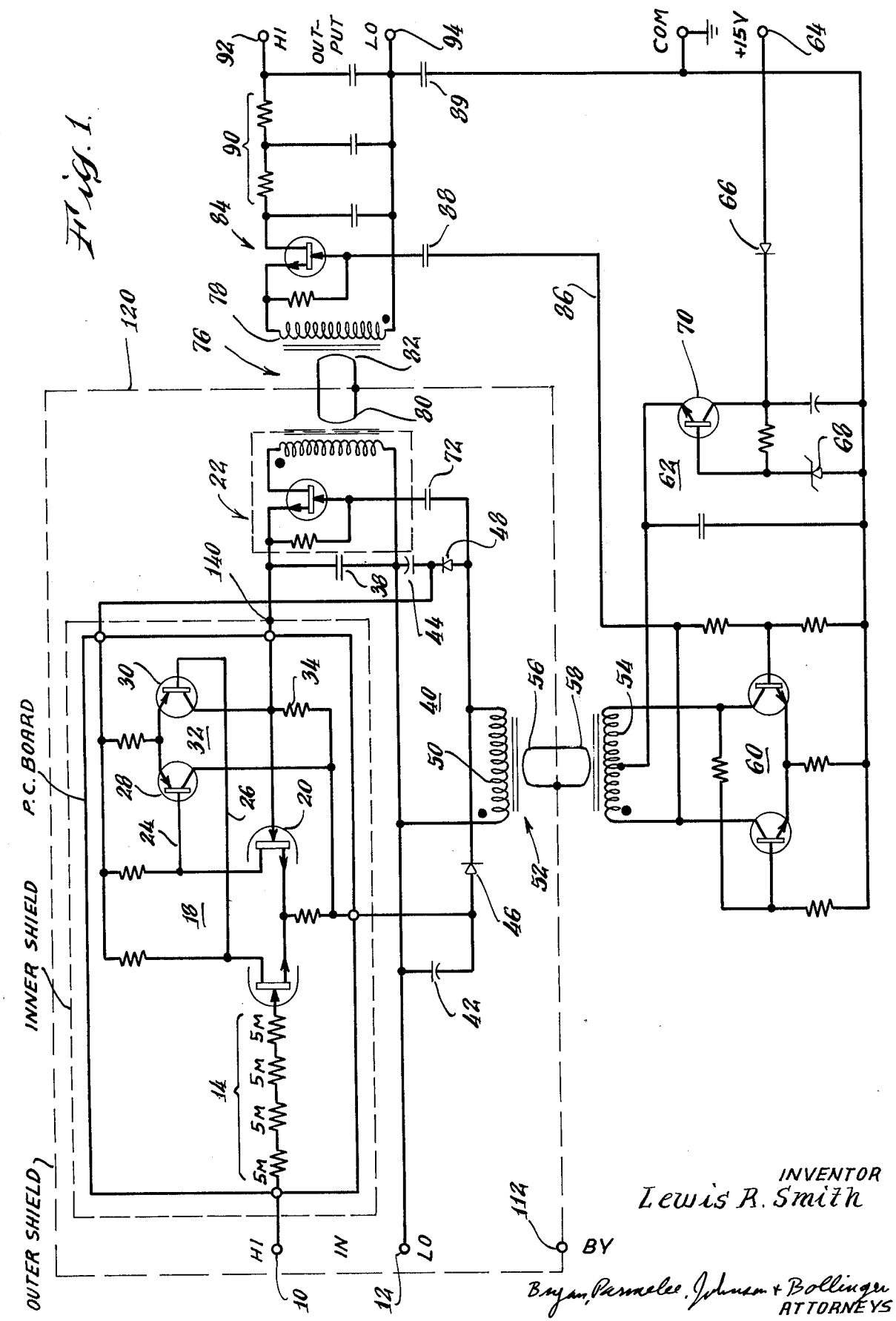
FIG. 1 is a schematic diagram showing the detailed interconnections of an amplifier embodying the present invention.

Referring now to the left-hand side of FIG. 1, the isolation amplifier includes an input section having a pair of inut terminals 10, 12 to which a signal source is to be connected. The upper input terminal 10 is connected through a series of four resistors 14 (e.g. 5 megohms each) to the non-inverting input element 16 of a balanced FET stage generally indicated at 18. The inverting input element 20 of this FET stage is connected to the amplifier output which in turn is connected to the upper terminal of the load 22 to be described subsequently. The lower input terminal 12 of the amplifier is connected to the lower terminal of this load. The FET input stage 18 provides a basically very high input impedance for the amplifier.

The signal developed by the FET input stage 18 is direct-coupled by leads 24, 26 to the bases 28, 30 of a differential transistor power amplifier stage 32. The output signal developed by this stage on resistor 34 is connected to the inverting input element 20 of the preceding FET stage so as to provide negative feedback to stabilize the gain of the amplifier. The amplifier stages 18 and 32 provide power amplification with a unity voltage gain.

The amplifier load 22 basically comprises an AC modulator arranged to produce an AC pulse signal having an amplitude corresponding to the magnitude of the DC signal on the input terminals 10, 12. Advantageously, this modulator is a halfwave FET circuit arranged as a switch in series with a transformer primary 36. A by-pass capacitor 38 also is connected to the amplifier output.

DC supply voltages for the active elements of amplifier stages 18 and 32 are derived from a floating rectifier power supply generally indicated at 40. This power supply comprises a pair of series-connected capacitors 42, 44 which are charged by alternate half-wave AC pulses supplied through diodes 46, 48 from a secondary winding 50 of an isolation transformer generally indicated at 52.

The transformer secondary winding 50 is coupled to the primary winding 54 by a pair of series-connected back-to-back single-turn windings 56, 58 to be referred to in more detail subsequently. This primary winding is energized by an AC oscillator generally indicated at 60, and providing, for example, an essentially square-wave output signal having a frequency of about 150 KHz. This oscillator, which is conventional in design, is furnished with DC power from a regulated supply generally indicated at 62 and energized by an external source voltage of about 15 volts applied to a terminal 64. Current from this external source flows through a diode 66 to a Zener diode 68 which controls the regulating action of a transistor 70.

The AC oscillator signal on the transformer secondary 50 also is coupled through a capacitor 72 to activate the half-wave FET modulator 22. As noted above, modulator 22 is in effect a switch connected in series between the DC signal from resistor 34 and the transformer primary 36. The switch is opened and closed alternately by the square-wave AC signal coupled from the transformer secondary 50, so as to create a modulated carrier in the primary winding 36.

This primary 36 forms part of a second isolation transformer generally indicated at 76 and similar to the transformer 52. Thus the primary 36 is coupled to the secndary 78 by a pair of series-connected back-to-back single-turn windings 80, 82, and develops in secondary 78 a modulated carrier the pulses of which have an amplitude corresponding to the magnitude of the DC signal on input terminals 10, 12.

The modulated AC signal on the secondary winding 78 is directed to a half-wave FET phase-sensitive demodulator 84 which serves to produce a DC output signal corresponding to the AC amplitude of the modulated carrier signal, and thereby corresponding to the original DC signal applied to input terminals 10, 12, but with a moderately higher power level. This demodulator is, like modulator 22, effectively a series switch, opened and closed alternately, in synchronism with the carrier frequency. The switching action is controlled by an AC signal from the oscillator 60 supplied thereto through a lead 86 and a series coupling capacitor 88 connecting to one end of primary 54. With this coupling capacitor 88, and a second coupling capacitor 89 to complete the circuit, the coupling circuit between the oscillator section and the demodulator section is non-conductive, i.e. it will not pass DC currents. The output of the demodulator is smoothed by an RC filter 90 and is supplied to the amplifier output terminals 92, 94.

Figure 2:
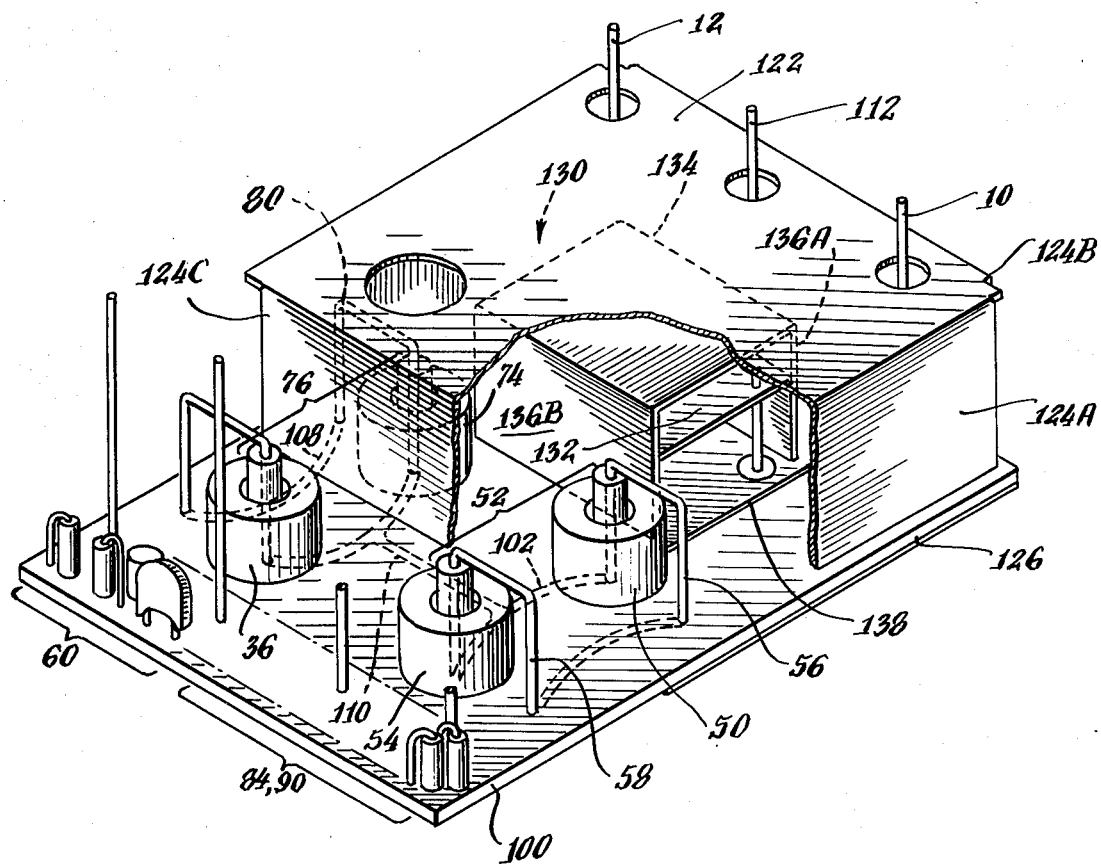
FIG. 2 is a view showing the physical disposition of certain portions of the amplifier.

Referring now also to FIG. 2, it will be seen that each of the isolation transformers 52, 76 comprises two separate cores, one for the primary and one for the secondary. Each core is made of magnetic material (ferrite) arranged as a toroid, and is wrapped with the coils of the corresponding winding. All of the cores are physically disposed with the toroidal axes perpendicular to the mounting board.

In a preferred embodiment, the cores were obtained from Indiana General Corporation, under their part number CF108-06. The ferrite material had a hig permeability, suitable for low-frequency applications. The windings 50, 54 had 25 and 50 turns respectively, while windings 36, 78 had 50 turns each.

The four single-turn windings 56, 58; 80, 82 consist of rigid metallic conductors each having a portion passing through the corresponding transformer core, parallel to the central (vertical) axis of the toroid. These vertical portions are surrounded by heavy tubular Teflon jackets, providing good electrical insulation. From the upper ends of the central vertical portions, the single-turn windings continue with horizontal portions, extending out over the sides of the cores, and joining additional vertical portions extending down alongside the cores parallel to the toroid axes.

All of the vertical portions of the single-turn windings pass through the printed circuit board 100 on which the amplifier is mounted. At the lower surface of this board, the bottom ends of the central vertical portions for each transformer are connected together by respective conductive elements (indicated in light outline at 102, 104) applied to the lower board surface. The bottom ends of the side vertical portions for each transformer similarly are connected by respective conductive elements 106, 108.

Thus it will be seen that each pair of series-connected single-turn windings defines a closed-circuit "intermediate winding" which loops about both of the associated transformer cores and provides inductive coupling between the primary and secondary windings thereon. Each of the single-turn windings almost completely encircles its corresponding core, but does not actually produce a shorted-turn effect, i.e. the windings do not nullify flux in the cores. The conductive elements 102, 104 are connected together by element 110, and are connected to a circuit "guard" terminal 112 (to be described) to maintain the single-turn windings at the guard potential.

A conductive metal shield box generally indicated at 120 is positioned around the parts of the amplifier circuitry which are conductively connected to the input terminals 10, 12. These amplifier parts include the transformer windings 36, 50. The shield 120 also surrounds the single-turn winding segments identified as 56 and 80, and which are associated by proximity to windings 36, 50.

The shield box 120 comprises an upper enclosure having a horizontal top plate 122 and four vertical sides or walls (124A, etc.) contiguous with the top plate. The lower edges of the four walls rest on non-conductive portions of the printed circuit board 100. The shield is completed by a bottom plate 126 of non-conductive material extending along the lower surface of the printed circuit board, and having on its lower surface a thin film of conductive material connected to the rear vertical walls 124B with a conductive connection (not shown) so that the entire shield is at the same potential.

The single-turn transformer coupling windings 56, 58; 80, 82 permit substantially physical separation between the corresponding primary and secondary windings, and thereby provide effective isolation between the windings. These single-turn windings also are connected to the shield 120, as by means of a conductive element (not shown in FIG. 2, but illustrated symbolically in FIG. 1) leading from winding element 104 to the common junction between the bottom plate 126 and rear wall 124B. The forward enclosure wall 124C extends down between the winding pair 50, 54 and also between the winding pair 36, 78, equidistant from the respective windings. The overall shielding effect reduces leakage capacity coupling to a very large degree, resulting in highly advantageous amplifier performance.

Further isolation is provided by an inner shield 130 substantially surrounding a second printed circuit board 132 carrying the circuitry making up the FET input stage 18 and the subsequent transistor stage 32. This inner shield includes an upper enclosure consisting of a top horizontal plate 134 and a pair of opposed vertical walls 136A, 136B integral therewith. The upper enclosure is conductively connected to a lower horizontal sield section 138 which is applied as a layer of conductive material to the upper surface of the main printed circuit board 100.

The inner shield 130 is connected at 140 to the conductor carrying the output signal of the FET amplifier 18. This maintains the shield at a potential essentially equal to that of the input terminals, but at a relatively low impedance level. The inner shield is especially advantageous in that it reduces substantially the capacitive coupling between ground and the right-hand end of the input resistor 14. This is very desirable because, without such reduced coupling, the high impedance (20 megohms) of the input resistor could under certain circumstances create adverse effects from leakage current, i.e. if the capacitive coupling from ground to that resistor were of normal magnitude.

Figure 3:
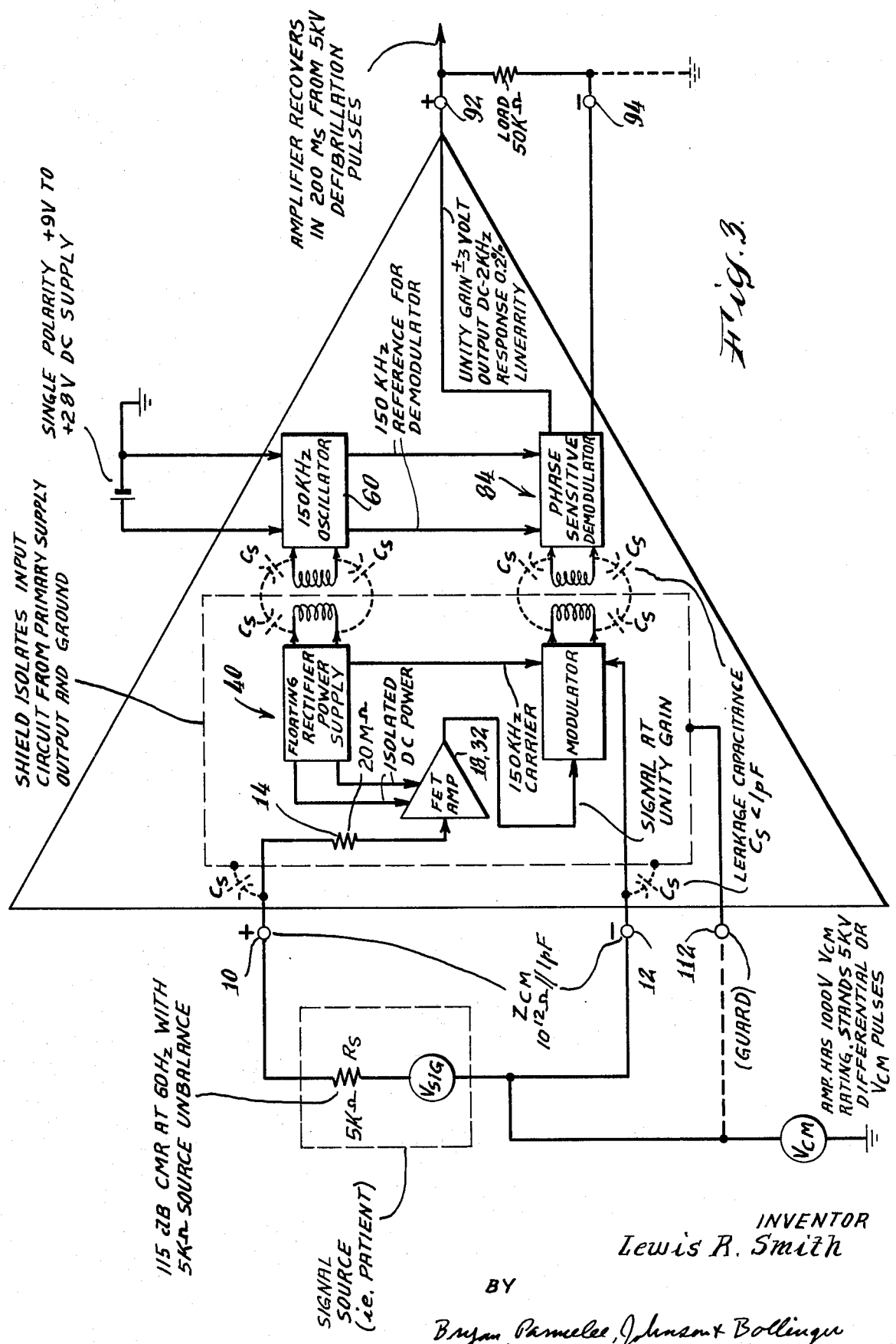
FIG. 3 is a symbolic block diagram showing the interconnections of the major elements of the amplifier.

As noted above, the single-turn windings 56, 58; 80, 82, and the outer shield 120, are connected to the guard input terminal 112. In making electrocardiogram measurements, for example, this guard terminal would be connected to the patient's body, e.g. at the lower portion of his leg. This provides desirable isolation, with common mode signals applied to both input terminals 10, 12 essentially equally, thus very nearly eliminating any response from such common mode signals. This characteristic is illustrated by the block diagram of FIG. 3, which shows the common mode signal ($V_{CM}$) connected between ground and the guard terminal 112.

No DC connection exists between the input terminals 10, 12 and any of the surrounding ground, output or power supply circuits. By virtue of the transformer isolation arrangement described above, the leakage resistance, as seen at the input, is at least $10^{12}$ ohms, and the three-terminal capacitive leakage is below 1 picofarad.

A further fail-safe protection feature resides in the twenty megohm resistance 14 in series with the non-inverting input element 16. Normally, the differential input resistance of the FET stage is about $10^{11}$ ohms which is adequate for patient protection when the amplifier is used for EKG applications. However, this differential resistance may be dramatically reduced if the FET gates are inadvertently forward biased, or in the event of serious semi-conductor damage, and thereby create a leakage path for possibly lethal currents. The twenty megohm series resistor sets a minimum fail-safe condition for input resistance, and holds leakage currents to a safe level even if the patient is "floating" at a potential as high as 220 volts (a typical line voltage amplitude in hospital opeating rooms) due to faulty equipment connected to the patient, or due to operator inadvertence.

In heart surgery, the amplifier used for EKG monitoring is not usually itself the source of electrocution danger. Instead, the amplifier may inadvertently provide the final connection between patient and ground through which the lethal currents leaked by other improperly grounded apparatus can flow. The patient typically is the focal point of a maze of pipes and tubes and mechanisms, many of which couple him to electrically driven pumps, heaters, operating table positioning motors, etc. If he is connected to ground, lethal leakage currents from such associated equipment may pass through him.

One possible such leakage path is from the amplifier inputs to ground. Even if the amplifier itself is not grounded, it is likely that display equipment, to which the amplifier's output is coupled, will be grounded. In the amplifier described hereinabove, dangerous leakage currents are effectively eliminated, due to the unique transformer isolation arrangement. For example, even if the patient is at a potential of 220 volts, a leakage current of less than about 2 microamps will flow.

Another possible leakage path is via the amplifier's differential input terminals. For example, if one EKG electrode is accidentally dropped to ground while the other remains connected to the patient's heart, a path is established for current flow through the amplifier input to ground. However, the amplifier described herein avoids dangerous leakage current levels due to its high differential input resistance. Note that even if the applied input potential is sufficient to forward bias the FET gates (which would otherwise create the described high differential resistance), the fail-safe twenty megohm resistor 14 will continue to bar seriously dangerous leakage current levels. This resistor also protects the input circuitry from permanent damage in the event of such overload conditions, such as when a high-voltage (e.g., 5000 volts) defibrillator pulse is applied to the patient.

Still another leakage path is from input-to-guard (shield) terminals. For example, small leakage, as from a power line, may establish apparently innocuous potential differences between different parts of the patient's body. If such potential difference is created between the patient's heart and a point on his body where the guard lead is connected, body voltages as low as 10 millivolts can circulate currents of 20 microamperes between EKG electrodes and a low-resistance input-to-guard path. However, the amplifier described above has very high input-to-guard impedance, because the conductive parts connected to the guard terminal are isolated from the other components of the amplifier. Thus, input-to-guard leakage currents are held well below the danger level.

Although a specific preferred embodiment of the invention has been described hereinabove in detail, it is desired to stress that this is for the purpose of illustrating the invention, and is not to be considered as necessarily limitative thereof, because it is apparent that various modifications within the scope of the invention can be made by those skilled in this art to meet the requirements of specific applications.

I claim:

1. A DC amplifier providing a high degree of isolation between input, output, ground and power circuits, so as to permit safe and accurate amplification of tiny DC electrical signals in applications such as monitoring of patients during medical operations and the like, said amplifier comprising:

an input section adapted to receive the DC input signal and including an a-c energized modulator to produce an AC signal corresponding to the DC input signal;

an output section to receive the AC signal from said input section and including a phase-sensitive demodulator to produce a corresponding relatively high-level DC output signal;

first circuit means non-conductively coupling said AC signal from said input section to said output section;

an oscillator section for pproducing an a-c energizing signal for said modulator and said demodulator;

second circuit means non-conductively coupling the a-c energizing signal from said oscillator to said input section to activate said modulator;

third circuit means coupling the a-c energizing signal from said oscillator to said output section to activate said demodulator;

said first non-conductive coupling circuit means further comprising:

first and second toroidal cores of magnetic material, said cores being physically separated by a substantial distance and each carrying a multi-turn winding inductively coupled to the magnetic material of the associated core; and conductor means forming a unitary, single turn, closed-loop linking said first and second toroidal cores and effectively coupling the magnetic paths thereof together inductively, said conductor means including generally rigid portions which extend through the central openings in both toroids, each centrally positioned within the corresponding opening to be spaced substantially from the inner surfaces of the corresponding toroid and its associated multiturn winding, the portions of said conductor means connecting to said generally rigid portions also being spaced substantially from the corresponding toroid and the associated winding, to provide low capacitive coupling and a desirably high voltage-breakdown characteristic between said conductor means and said multi-turn windings, the arrangement providing that both said cores are encircled by said single-turn closed loop;

whereby the conductive path formed by said closed-loop serves as a short-circuiting turn to resist any net changes in magnetic flux through the loop as a whole so as to cause the flux variations in said second toroidal core always to be equal to the flux variations in said first toroidal core, thereby effecting a transformer-like coupling between said first and second cores while providing for spatial separation with relatively low overall capacitive coupling and relatively high voltage-breakdown characteristics.

2. Apparatus as claimed in claim 1, wherein said second non-conductive circuit means is the same as said first non-conductive means and comprises third and fourth toroidal cores each with multi-turn windings and linked by second conductor means forming a second unitary, single-turn, closed-loop linking said third and fourth cores together inductively, with the second conductor means including generally rigid portions which extend through the central opepnings in both said third and fourth toroids and are centrally positioned within said openings thereof to be spaced substantially from the corresponding toroid and its associated multi-turn winding.

3. Apparatus as in claim 2, including a conductive shield having a wall extending down between said first and second cores, and between said third and fourth cores.

4. Apparatus as in claim 3, wherein said toroidal cores are mounted on one side of a circuit board which also supports said conductive shield;

said first and second conductor means including further portions which pass from the toroidal core openings through said circuit board to the other side thereof and extend along said other circuit board side to establish said closed-loops without physical or electrical interference with said conductive shield wall.

5. Apparatus as in claim 1, wherein said conductor means carries heavy tubular jackets of insulating material in the portions thereof passing through the cores, to augment the high voltage-breakdown characteristic of the coupling arrangement.

6. A solid-state DC amplifier providing a high degree of conductive isolation between its input and output and capable of superior performance in amplifying very low-level DC input signals with minimal interference due to capacitive coupling from sources of stray signals, said amplifier comprising:

an input section conductively isolated from all other sections of the amplifier;

first circuit means in said input section comprising a DC amplifier stage adapted to receive the DC input signal and to produce an intensified DC signal corresponding to said input signal, said amplifier comprising a semi-conductor providing a very high input impedance so as to avoid drawing any significant current from the source of said DC input signal;

second circuit means in said input section conductively connected to the output of said first DC amplifier stage to receive said intensified DC signal, said second circuit means including a modulator adapted to be activated by an a-c energizing signal to produce an AC output signal having an amplitude corresponding to the magnitude of said intensified DC signal;

third circuit means in said input section comprising a d-c voltage supply having rectifier means adapted to receive an a-c energizing signal and to produce a corresponding d-c power-supply voltage;

said third circuit means including means conductively connected between said rectifier means and said DC amplifier stage to direct said d-c power-supply voltage to said DC amplifier stage to furnish operating power thereto;

an output section conductively isolated from, and inductively coupled to, said input section to receive the AC output signal produced thereby;

a demodulator forming part of said output section and responsive to said AC output signal for producing a DC output signal having a magnitude corresponding to the amplitude of said AC output signal;

said demodulator including means to receive an a-c energizing signal synchronized with said AC output signal for activating said demodulator to produce said DC output signal;

an a-c power section conductively isolated from said input section;

an oscillator forming part of said a-c power section to produce an a-c energizing signal;

d-c supply circuit means for energizing said oscillator and arranged to receive a supply current from an external source for activating said oscillator;

first non-conductive means for coupling said a-c energizing signal from said a-c power section to said input section, second means for coupling said a-c energizing signal from said a-c power section to said output section; and means in said input and outut sections to supply the a-c energizing signal from said oscillator to: (1) said d-c supply so as to develop from said rectifier means the power supply voltage for said DC amplifier stage, (2) said modulator in said input section, and (3) said demodulator in said output section, whereby said oscillator provides operational power for all of the circuits of said input and output sections including d-c power for said DC amplifier stage.

7. An isolation amplifier especially adapted for use in medical applications where it is essential that no high level currents be permitted to flow into the amplifier input circuit, as from a patient's body to which the amplifier is connected, said amplifier comprising:
an input section having a pair of input terminals to which the signal source is to be connected;
said input section having circuit elements coupled to said input terminals comprising an amplifier element of solid-state material having at least hundreds of megohms normal resistance but subject to damage which could reduce the input resistance of the element to a much lower level;
said input section further including an AC modulator coupled to the output of said amplifier element to produce a modulated AC signal corresponding to the DC input signal applied to said input terminals;
an output section conductively isolated from said input section;
said output section including a demodulator arranged to receive the modulated AC signal from said input section and to produce a DC output signal corresponding to said DC input signal;
non-conductive circuit means coupling said modulated AC signal from said input section to said output section; and
at least one resistor of multi-megohm resistance connected between at least one of said input terminals and said solid-state amplifier element to provide a fail-safe protection against the flow of abnormally high currents through said input terminals to the solid-state material of said amplifier element in the event of either (1) breakdown of the solid-state material from any cause or (2) the application to said input terminals of an extremely high voltage such as a defibrillator pulse applied to a patient to stimulate the heart.

* * * * *